(12) United States Patent
Choisy et al.

(10) Patent No.: US 11,554,090 B2
(45) Date of Patent: Jan. 17, 2023

(54) MAKEUP COMPOSITION COMPRISING A BLUE PIGMENT

(71) Applicant: L'OREAL, Paris (FR)

(72) Inventors: Patrick Choisy, Montlouis sur Loire (FR); Martin Michel, Lausanne (CH)

(73) Assignee: L'OREAL, Paris (FR)

( * ) Notice: Subject to any disclaimer, the term of this patent is extended or adjusted under 35 U.S.C. 154(b) by 1506 days.

(21) Appl. No.: 14/422,868

(22) PCT Filed: Aug. 22, 2013

(86) PCT No.: PCT/EP2013/067459
§ 371 (c)(1),
(2) Date: Feb. 20, 2015

(87) PCT Pub. No.: WO2014/029842
PCT Pub. Date: Feb. 27, 2014

(65) Prior Publication Data
US 2015/0216776 A1    Aug. 6, 2015

Related U.S. Application Data

(60) Provisional application No. 61/724,570, filed on Nov. 9, 2012.

(30) Foreign Application Priority Data

Aug. 23, 2012 (FR) ...................... 1257954

(51) Int. Cl.
| | | |
|---|---|---|
| A61K 8/49 | (2006.01) |
| A61Q 1/10 | (2006.01) |
| A61Q 1/02 | (2006.01) |
| C09B 63/00 | (2006.01) |
| A61K 8/60 | (2006.01) |
| C09B 61/00 | (2006.01) |
| A61K 8/19 | (2006.01) |
| A61K 8/9789 | (2017.01) |
| A61K 8/9794 | (2017.01) |

(52) U.S. Cl.
CPC .............. *A61K 8/498* (2013.01); *A61K 8/19* (2013.01); *A61K 8/602* (2013.01); *A61K 8/9789* (2017.08); *A61K 8/9794* (2017.08); *A61Q 1/02* (2013.01); *A61Q 1/10* (2013.01); *C09B 61/00* (2013.01); *C09B 63/005* (2013.01); *A61K 2800/43* (2013.01); *A61K 2800/432* (2013.01)

(58) Field of Classification Search
None
See application file for complete search history.

(56) References Cited

U.S. PATENT DOCUMENTS

| | | | | |
|---|---|---|---|---|
| 4,481,226 A | * | 11/1984 | Crosby | ................... C09B 61/00 426/250 |
| 2004/0156802 A1 | * | 8/2004 | Iwasaki | ................ A61K 8/0212 424/70.1 |
| 2008/0095719 A1 | * | 4/2008 | Herrmann | ................ A61K 8/97 424/48 |

FOREIGN PATENT DOCUMENTS

| | | |
|---|---|---|
| EP | 1798262 A1 | 6/2007 |
| EP | 2 633 849 A | 9/2013 |
| JP | S56 035968 A | 4/1981 |
| JP | 2004 091758 A | 3/2004 |
| JP | 2012-092030 A | 5/2012 |

OTHER PUBLICATIONS

Salas et al., "Reactions of Anthocyanins and Tannins in Model Solutions", J. Agric. Food Chem., 2003, 51, 7951-7961.
Malien-Aubert et al., "Color Stability of Commercial Anthocyanin-Based Extracts in Relation to the Phenolic Composition. Protective Effects by Intra- and Intermolecular Copigmentation", J. Agric. Food Chem., 2001, 49, 170-176.

* cited by examiner

*Primary Examiner* — David J Blanchard
*Assistant Examiner* — Sarah J Chickos
(74) *Attorney, Agent, or Firm* — Polsinelli PC

(57) ABSTRACT

The invention relates to a cosmetic composition comprising a blue dye powder containing an anthocyan, a metal ion and tannic acid and a cosmetic additive. The invention also relates to a process for making up keratin materials by applying the cosmetic composition to the keratin materials.

13 Claims, No Drawings

MAKEUP COMPOSITION COMPRISING A BLUE PIGMENT

CROSS REFERENCE TO RELATED APPLICATIONS

This application is a National Phase filing under 35 U.S.C. § 371 of PCT/EP2013/067459 filed on Aug. 22, 2013; and this application claims priority to Application No. 1257954 filed in France on Aug. 23, 2012; and this application claims priority to U.S. Provisional Application No. 61/724,570 filed on Nov. 9, 2012. The entire contents of each application are hereby incorporated by reference.

The present invention relates to a process for making up human keratin materials using a blue dye powder comprising an anthocyan.

In recent years, there has been increasing interest in natural compounds that can be used as dyestuffs, especially in the cosmetics sector.

The available colour range among natural dyes is not as wide as that of synthetic dyes, and many natural dyes show poor stability when exposed to light. In particular, there are very few natural blue dyes, and these dyes are not sufficiently photostable: their hue fades and does not produce a very attractive colour effect.

The aim of the present invention is thus to provide a blue colour powder which shows good photostability without any fading of the colour hue.

The inventors have discovered that such a dye powder is obtained by stabilizing anthocyans in the presence of certain metal ions and tannic acid.

More specifically, the present invention relates to a process for making up keratin materials, comprising the application to the keratin materials of a dye powder having a blue colour comprising at least one anthocyan, metal ions chosen from the group of ions derived from Al(III), Ca(II), Cu(II), Fe(II), Fe(III), Mg(II), Mn(II) and Zn(II) and mixtures thereof, tannic acid or a gallotannin derivative thereof, or mixtures thereof.

The invention also relates to a cosmetic composition comprising, in a physiologically acceptable medium, (i) a dye powder having a blue colour comprising at least one anthocyan, metal ions chosen from the group of ions derived from Al(III), Ca(II), Cu(II), Fe(II), Fe(III), Mg(II), Mn(II) and Zn(II) and mixtures thereof, tannic acid or a gallotannin derivative thereof, or mixtures thereof, and (ii) a cosmetic additive chosen from fragrances, preserving agents, film-forming polymers, fillers, UV-screening agents, thickeners, silicone oils, plant oils, liquid paraffins, waxes, moisturizers, vitamins, proteins, ceramides, antioxidants, free-radical scavengers, organic solvents, mineral pigments (titanium dioxide or iron oxides) and nacres.

Blue is the hue of that portion of the visible spectrum lying between green and indigo. One method of measuring colour proposed by the Commission Internationale de l'Éclairage (CIE) is the CIE 1976 L*a*b* colour scale, herein abbreviated as CIELAB (CIE Technical Report, Colorimetry $2^{nd}$ Edition, CIE 15.2—1986, corrected reprint 1996). The CIELAB colour space is produced by plotting the quantities L*, a*, b* in rectangular coordinates. The L* coordinate of an object is the lightness intensity as measured on a scale from 0 (black) to 100 (absolute white). The a* and b* coordinates have no specific numerical limits. The parameter a* runs from pure green (negative a*) to pure red (positive a*), while b* runs from pure blue (negative b*) to pure yellow (positive b*).

The hue angle $h_{ab}$ is calculated from a* and b* values as:

$h_{ab}=\arctan(b*/a*)$ where $h_{ab}$ lies between 0° and 90° if b* and a* are both positive, between 90° and 180° if b* is positive and a* is negative, between 180° and 270° if b* and a* are both negative, and between 270° and 360° if b* is negative and a* is positive.

"Blue" within the scope of the present invention refers to a CIELAB hue angle $h_{ab}$ between 210° and 325°, for example between 225° and 315°.

The dye powder used according to the invention comprises at least one anthocyan.

Anthocyans are, as is known, anthocyanidol glycosides (Jin-Ming Kong et al., Phytochemistry, 64, 923-933 (2003)).

More than 500 different anthocyans exist in nature. Their main differences relate to the number of hydroxyl groups and of methoxy groups, the nature and number of sugar units present, the aliphatic or aromatic carboxylate groups attached to the sugars in the molecule and the position of these bonds (A Castañeda-Ovando et al., Food Chemistry, 113, 859-871 (2009)).

Anthocyanidols are compounds of formula (I) below:

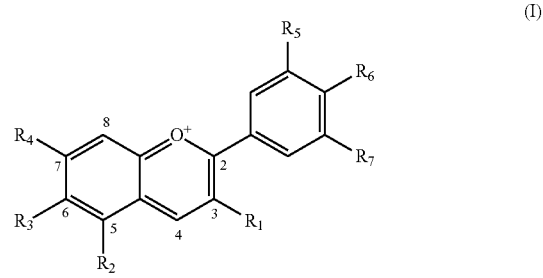

in which the radicals $R_1$ to $R_7$ independently denote H, OH or OMe.

The six most common anthocyanidols are indicated in Table 1 below with their name, abbreviation and substituents on formula (I) described previously.

TABLE 1 common anthocyanidols

| Name (abbreviation) | $R_1$ | $R_2$ | $R_3$ | $R_4$ | $R_5$ | $R_6$ | $R_7$ |
|---|---|---|---|---|---|---|---|
| Cyanidin (Cy) | OH | OH | H | OH | OH | OH | H |
| Delphinidin (Dp) | OH | OH | H | OH | OH | OH | OH |
| Pelargonidin (Pg) | OH | OH | H | OH | H | OH | H |
| Peonidin (Pn) | OH | OH | H | OH | OMe | OH | H |
| Petunidin (Pt) | OH | OH | H | OH | OMe | OH | OH |
| Malvidin (Mv) | OH | OH | H | OH | OMe | OH | OMe |

On account of their abundance, the sugars bonded to the anthocyanidols are especially glucose, rhamnose, galactose, xylose, arabinose and glucuronic acid.

The main glycoside derivatives in nature are 3-monosides, 3-biosides, 3,5-diglucosides and 3,7-diglucosides. The anthocyans may also be acetylated, and the sugars may be acylated with methyl or malonic, p-coumaric acid, ferulic acid, sinapylic acid or caffeic acid substituents (F. J. Francis, Colorants, p. 56, Eagan Press (1999)). The most common anthocyan is cyanidin-3-O-glucoside.

Advantageously, the anthocyans used according to the present invention may be chosen from those of formula (I) in which $R_1$, $R_2$ and $R_4$ independently denote H, OH, OMe, a sugar unit or an acylated sugar unit (acyl group derived from malonic acid, p-coumaric acid, ferulic acid or caffeic acid) and $R_3$, $R_5$, $R_6$ and $R_7$ independently denote H, OH or OMe.

The anthocyans may be of natural or synthetic origin.

A certain number of plants are naturally rich in anthocyans. Examples that may be mentioned include black carrot, elderberry, hibiscus, blackcurrant, purple corn and black potato. The four main anthocyans present in blackcurrant are cyanidin-3-O-rutinoside, cyanidin-3-O-rutinoside, delphinidin-3-O-glucoside and delphinidin-3-O-rutinoside. Black grape and red cabbage are the two most important sources of anthocyans in nature. The anthocyanidin units of the anthocyans present in black grape are cyanidin, peonidin, malvidin, petunidin and delphinidin; and the organic acids present are acetic acid, coumaric acid and caffeic acid. The only sugar present is glucose (F. J. Francis, Colorants, p. 56, Eagan Press (1999)). A grape anthocyan, malvidin-3,5,-diglucoside, corresponds to formula (II) below, in which Glu is glucose and Me is the methyl radical.

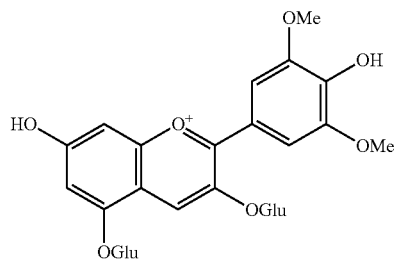

(II)

The anthocyans used according to the present invention may be cyanidin-3-O-rutinoside, delphinidin-3-O-rutinoside, cyanidin-3-O-glucoside or malvidin-3,5,-O-diglucoside.

Seven of the anthocyans present in red cabbage are described in formula (III). These anthocyans comprise the basic structure cyanidin-3-diglucoside, but comprise different groups $R_1$ and $R_2$. The groups $R_1$ and $R_2$ of these seven anthocyans are sinapyl, ferulyl or p-coumaryl, as indicated in Table 1.

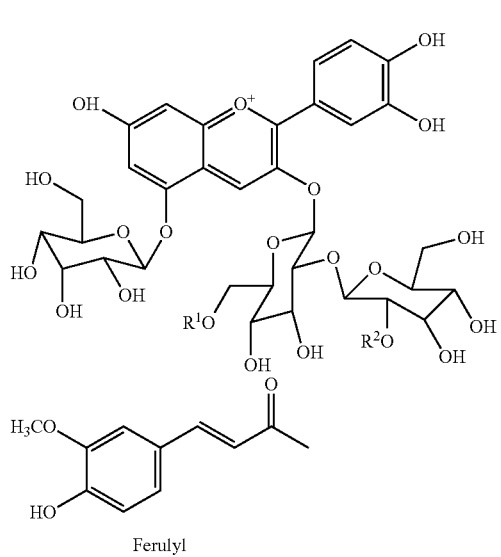

(III)

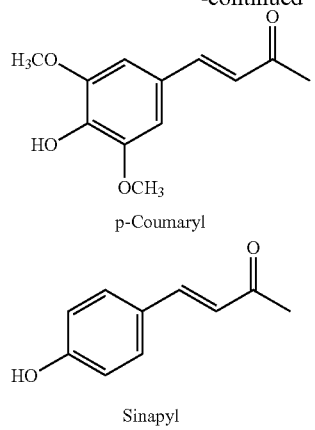

TABLE 1

| | $R_1$ | $R_2$ |
|---|---|---|
| A | H | Sinapyl |
| B | Sinapyl | H |
| C | Ferulyl | H |
| D | p-Coumaryl | H |
| E | Sinapyl | Sinapyl |
| F | Ferulyl | Sinapyl |
| G | p-Coumaryl | Sinapyl |

The anthocyans used according to the present invention may be one or more of the cyanidin-3-diglucosides A to G described previously.

The anthocyans may be added in the form of plant matter or an extract of plant matter. It may be advantageous to avoid unnecessary purification of the plant matter. Thus, the other components of the plant matter may be advantageous for the dye powder. For example, other components of the plant matter, for instance flavonoids, are advantageous for their antioxidant properties.

The plant matter may be, for example, legumes, fruit or flowers. The plant matter may be chosen from red cabbage, red onion, purple potato, grape, cranberry, strawberry, raspberry, aronia, black soybean, blackcurrant, elderberry, hibiscus, radish, gooseberry, bilberry, cherry, aubergine, black carrot and black rice.

The anthocyan may be present in the dye powder in a content ranging from 0.05% to 50% by weight, preferably ranging from 0.3% to 25% by weight and preferentially ranging from 5% to 15% by weight relative to the total weight of solids of the dye powder.

The dye powder according to the invention comprises metal ions chosen from ions derived from Al(III), Ca(II), Cu(II), Fe(II), Fe(III), Mg(II), Mn(II) and Zn(II), and mixtures thereof. The metal ions are preferably chosen from ions derived from Fe(II), Fe(III) and Mg(II), and mixtures thereof. The ion derived from Fe(II) is preferred.

These metal ions make it possible to stabilize the anthocyans by complex formation and by effecting a bathochromic shift towards blue shades.

The salts of these metal ions are well known, with anions such as gluconate, chloride, sulfate, hydroxide and acetate. For example, calcium gluconate contains the ($Ca^{2+}$) ion derived from Ca(II); magnesium chloride, $MgCl_2$, or magnesium gluconate contains Mg(II) ions ($Mg^{2+}$); ferrous sulfate, $FeSO_4$, iron gluconate $(C_6H_{11}O_7)_2Fe$ contains Fe(II)

ions ($Fe^{2+}$); ferric sulfate, $Fe_2(SO_4)_3$, contains Fe(III) ions ($Fe^{3+}$); and aluminium sulfate, $Al_2(SO_4)_3$, contains Al(III) ions ($Al^{3+}$).

The metal ions may be present in the dye powder in a metal ion/anthocyan weight ratio ranging from 0.01/1 to 10/1 and preferably ranging from 0.05/1 to 5/1 by weight.

The dye composition comprises tannic acid or a gallotannin derivative thereof, or mixtures thereof.

Tannic acid (or hydrolysable gallotannin) is a mixture of polygalloyl glucoses or of polygalloyl quinic acid esters with a number of galloyl units per molecule ranging from 2 to 12, dependent on the plant source used to extract the tannic acid.

The chemical formula of commercial tannic acid that is usually given is $C_{76}H_{52}O_{46}$, which corresponds to decagalloyl glucose.

The term "gallotannin derivatives of tannic acid" means the polygalloyl glucose compounds and the polygalloyl quinic acid esters described previously.

Commercial tannic acid is usually extracted from tara husk seeds (*Caesalpinia spinosa*), gall nuts or excrescences thereof which form on the young branches of *Quercus infectoria* and belonging to the species of *Quercus L.* (Fam. Fagaceae), or gall nuts of various species of *sumach.*

Tannic acid or a gallotannin derivative thereof, and mixtures thereof, may be present in the dye powder in a tannic acid or gallotannin derivative/anthocyan weight ratio ranging from 0.05/1 to 20/1 and preferably ranging from 0.1/1 to 10/1.

In addition to the ingredients mentioned previously, the dye powder may comprise additional ingredients as described below.

The dye powder may comprise an amino acid, which may be chosen from taurine, proline and arginine. This amino acid acts as a bathochromic agent.

The amino acid may be present in the dye powder in an amino acid/anthocyan weight ratio ranging from 0.1/1 to 25/1, preferably ranging from 0.5/1 to 20/1 and preferentially ranging from 1/1 to 16.5/1.

The dye powder may comprise a phospholipid, and in particular phosphatidylcholine (also known as lecithin). This phospholipid allows a good interaction between the anthocyan, the metal ions and the tannic acid.

Phospholipids are a class of lipids which are predominant components of cell membranes and which may form lipid bilayers. A phospholipid molecule is constructed with four components: fatty acids, a backbone onto which the fatty acids are attached and a phosphate ester.

The phospholipid backbone may be glycerol or sphingosine.

Glycerol-based phospholipids are known as phosphoglycerides (Biochemistry 5$^{th}$ Edition, J. Berg et al., W.H. Freeman & Co (2002)). Examples of phospholipids that may be mentioned include phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphoryl choline, ceramide phosphorylethanolamine and ceramide phosphoryl glycerol.

Phospholipids are one of the constituents of lecithin. Lecithin is present in egg yolk and may also be extracted from seed oils.

The phospholipids used in the present invention may be a sunflower or soybean lecithin.

The main phospholipids of soybean or sunflower lecithin are phosphatidylcholine, phosphatidylinositol, phosphatidylethanolamine and phosphatidic acid.

Preferably, the phospholipid may be phosphatidylcholine. Use is made, for example, of the product sold under the trade name Ultralec by the company ADM.

The phospholipid may be present in the dye powder in a phospholipid/anthocyan weight ratio ranging from 0.1/1 to 50/1 and preferably ranging from 0.5/1 to 30/1.

The composition may comprise a monocarboxylic or dicarboxylic acid containing from 2 to 6 carbon atoms, chosen especially from acetic acid, malic acid and tartaric acid. This acid is advantageously present to adjust the pH of the dye composition preparation to between 3.5 and 8. Advantageously, the pH of the dye preparation is between 3.5 and 7, preferably between 4 and 6 and preferentially between 4 and 5.5.

The dye powder may be prepared in a first step by mixing in water the anthocyan (especially in plant extract form), while adjusting the pH to between 3.5 and 8.0, the metal ions in salt form, the tannic acid or gallotannin derivatives thereof and the other additional ingredients.

In a second step, the solid phase of the mixture obtained in the first step is isolated, especially by centrifugation, and then frozen, and is then dried, for example by lyophilization to recover the dye powder. Alternatively, a support such as maltodextrin may be added to the mixture obtained in the first step and the composition may be atomized to recover a dye powder.

The cosmetic composition comprising the dye powder also comprises a physiologically acceptable medium, i.e. a medium that is compatible with human keratin materials and/or fibres, for instance, in a non-limiting manner, the skin, mucous membranes, the nails, the scalp and/or the hair.

The composition according to the invention may also contain cosmetic additives as described previously.

The amounts of these various additives are those conventionally used in the cosmetics field, and may range, for example, from 0.01% to 30% of the total weight of the composition. In general, the amounts are adjusted as a function of the formulation prepared.

A cosmetic composition according to the invention may be in the form of a makeup product for the hair (in particular for coloured coating of the hair), the eyelashes, the eyebrows, the skin, the lips or the nails.

Other characteristics and advantages of the invention will emerge more clearly from the examples that follow, which are given as non-limiting illustrations. In the text hereinbelow or hereinabove, the proportions are given as weight percentages, unless otherwise indicated.

EXAMPLES 1 TO 9

Blue pigments were prepared from the following compositions:

|  | Anthocyan (g/l) (extract of bilberry) | Acetate buffer (0.01M) | Malic acid (g/l) | FeSO4 (g/l) | MgSO4 (g/l) | Tannic acid (g/l) | Phosphatidylcholine (g/l) | Proline (g/l) |
|---|---|---|---|---|---|---|---|---|
| Pigment 1 | 3 | 1 |  | 9 |  | 3 | 3.4 |  |
| Pigment 2 | 3 | 1 |  | 18 |  | 3 | 3.4 |  |

-continued

| | Anthocyan (g/l) (extract of bilberry) | Acetate buffer (0.01M) | Malic acid (g/l) | FeSO4 (g/l) | MgSO4 (g/l) | Tannic acid (g/l) | Phosphatidylcholine (g/l) | Proline (g/l) |
|---|---|---|---|---|---|---|---|---|
| Pigment 3 | 3 | 1 | | 9 | | 3 | | |
| Pigment 4 | 3 | 1 | | 9 | 9 | 3 | 3.4 | 3 |
| Pigment 5 | 3 | 1 | 3 | 18 | | 3 | | 3 |
| Pigment 6 | 3 | 1 | 3 | 18 | | 12 | | |
| Pigment 7 | 3 | 1 | 3 | 18 | | 24 | | |
| Pigment 8 | 3 | 1 | | 18 | | 3 | | |
| Pigment 9 | 3 | 1 | | 18 | | 6 | | |

The following solutions were first prepared in 0.1 M pH 5 sodium acetate buffer in deionized water.

Bilberry extract: mixture of aqueous-alcoholic extract of bilberry fruit and of maltodextrin (bilberry fruit PE 25% anthocyanosides from Naturex): 0.2 g of anthocyan active material in 50 ml of buffer Malic acid: 0.24 g in 20 ml of buffer Tannic acid: 0.39 g in 20 ml of buffer Iron sulfate: 0.14 g in 20 ml of buffer Magnesium sulfate: 0.18 g in 20 ml of buffer Phosphatidylcholine (Ultralec® U from ADM): 2.4 g in 20 ml of buffer Proline: 0.27 g in 20 ml of buffer Pigment preparation method:

The bilberry extract placed in the buffer was mixed with iron sulfate or magnesium sulfate and optionally with malic acid; the mixture was stirred for 2 hours in the darkness, at 25° C.; tannic acid was then added, and the mixture was then stirred for a further 2 hours under the same conditions; next, the mixture was heated for 3 hours at 75° C. Phosphatidylcholine and proline were then optionally added, and the mixture was stirred for 72 hours at 25° C.

Next, the mixture was optionally centrifuged to recover the final solid phase. This solid phase was then frozen at -22° C. and then freeze-dried.

Blue pigments were thus recovered.

EXAMPLE 10

A blue pigment was prepared according to the following procedure:

1.5 kg of red cabbage extract (Red Cabbage Anthocyanins ELCHRO7017 from Diana Naturals) were diluted in 8 litres of water and cooled to 4° C. 270 g of disodium hydrogen phosphate were added slowly and the pH was measured. The pH of the mixture was adjusted to about 5.5 by adding sodium bicarbonate. With stirring, 195 g of iron sulfate heptahydrate were added. The pH was measured and adjusted to be between 5.5 and 6.0 by addition of sodium bicarbonate. The mixture was stirred for 2 hours at a temperature of 4° C. 170 g of tannic acid (Ajinomoto ominichem) were dissolved in water and added slowly to the mixture. After this addition, the pH was checked and adjusted to between 5.5 and 6.0. The total of the sodium bicarbonate additions was 100 g. The total volume of the mixture was adjusted to 10 litres and stirred for 16 hours at 4° C. 1 kg of maltodextrin 20 DE was dissolved in the mixture and then pasteurized at 75° C. for 1 hour. The mixture was cooled and stirred for 48 hours at 4° C. and was then atomized to obtain a powder. A blue pigment was thus obtained.

EXAMPLE 11

Study of the Photostability of the Blue Pigments

The photostability of the pigments prepared in Examples 1 to 10 was measured according to the following protocol:

The water-in-oil emulsion having the following composition was prepared:

5% of pigment to be tested 6.55% of mixture of oxyethylenated polymethylcetyl dimethyl methylsiloxane, polyglyceryl isostearate (4 mol OE) and hexyl laurate (Abil WE 09 from Evonik-Goldschmidt)

0.51% of ethylene glycol acetyl stearate 0.03% of 2-oleamido-1,3-octadecanediol 5.82% of smectite in cyclopentadimethylsiloxane and ethanol (18/77/5) (Bentone Gel VS 5 V from Elementis)

10.35% of cyclopentadimethylsiloxane 2.91% of dimethicone 10 cSt 1.89% of isododecane 0.7% of magnesium sulfate 5% of propylene glycol qs preserving agents qs 100% of water The emulsion prepared was spread onto a contrast card.

The emulsion containing the pigment to be tested was applied to a 50 µm thick Erichsen contrast card ref. Typ 24/5 and was then left to dry at room temperature for 24 hours; the colour (measurement at t0 of L0, a0, b0) of the deposit obtained spread on the white part of the contrast card was measured at three points using a Minolta CM2600d colorimeter.

The deposit obtained was then subjected to irradiation under a Lot Oriel sun simulator for 1 hour (power 1600 W).

After irradiation, the colour of the deposit spread on the white part of the contrast card was measured with the colorimeter, taking care to avoid the zones previously read for the measurement at t0 (measurement at t1 of L1, a1, b1).

The photostability is determined by calculating the difference ΔE between the colour measurements before and after irradiation performed on the white background of the contrast card:

$$\text{Photostability} = \Delta E = ((L1^* - L0^*)^2 + (a1^* - a0^*)^2 + (b1^* - b0^*)^2)^{1/2}$$

The photostability is proportionately better the closer to 0 value of the colour difference ΔE thus determined.

The following results were obtained:

| Pigment tested | ΔE photostability |
|---|---|
| Ex. 1 | 3.91 |
| Ex. 2 | 3.26 |
| Ex. 3 | 3.80 |
| Ex. 4 | 3.43 |
| Ex. 5 | 1.56 |
| Ex. 6 | 1.88 |
| Ex. 7 | 0.55 |
| Ex. 8 | 2.12 |
| Ex. 9 | 0.54 |
| Ex. 10 | 2.02 |

The results obtained show that the pigments of Examples 1 to 10 have good photostability (ΔE<4).

EXAMPLE 12

Example of Eyeshadow

| | |
|---|---|
| Magnesium stearate | 4% |
| Talc | 30% |
| Glyceryl triisostearate | 5% |
| Hydrogenated polydecene | 5% |
| Blue pigment | qs 100% |

The eyeshadow applied to the eyelids has a beautiful blue colour.

The invention claimed is:

1. Process for making up keratin materials, comprising the application to the keratin materials of a dye powder having a blue colour comprising at least one anthocyan, metal ion chosen from the group of ions derived from Al(III), Ca(II), Cu(II), Fe(II), Fe(III), Mg(II), Mn(II) and Zn(II) and mixtures thereof, tannic acid or a gallotannin derivative thereof, or mixtures thereof, wherein the metal ion is present in the dye powder in a metal ion/anthocyan ratio ranging from 3/1 to 10/1.

2. Process according to the claim 1, wherein the anthocyan is a compound of formula (I):

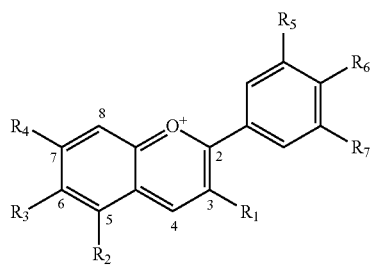

in which $R_1$, $R_2$ and $R_4$ independently denote H, OH, OMe, a sugar unit or an acylated sugar unit (acyl group derived from malonic acid, p-coumaric acid, ferulic acid or caffeic acid) and $R_3$, $R_5$, $R_6$ and $R_7$ independently denote H, OH or OMe.

3. Process according to claim 1, wherein the anthocyan is derived from plant matter chosen from red cabbage, red onion, purple potato, grape, cranberry, strawberry, raspberry, aronia, black soybean, blackcurrant, elderberry, hibiscus, radish, gooseberry, bilberry, cherry, aubergine, black carrot and black rice.

4. Process according to claim 1, wherein the metal ions are chosen from ions derived from Fe(II), Fe(III) and Mg(II), and mixtures thereof.

5. Process according to claim 1, wherein the anthocyan is present in the dye powder in a content ranging from 0.05% to 50% by weight relative to the total weight of solids of the dye powder.

6. Process according to claim 1, wherein the tannic acid or a gallotannin derivative thereof, or mixtures thereof, is present in the dye powder in a tannic acid or gallotannin derivative/anthocyan weight ratio ranging from 0.05/1 to 20/1.

7. Process according to claim 1, wherein the dye powder comprises an additional ingredient chosen from:
an amino acid chosen from taurine, proline and arginine;
a phospholipid;
a monocarboxylic or dicarboxylic acid containing from 2 to 6 carbon atoms.

8. Process according to claim 1, wherein the anthocyan is present in the dye powder in a content ranging from 0.3% to 25% by weight relative to the total weight of solids of the dye powder.

9. Process according to claim 1, wherein the anthocyan is present in the dye powder in a content ranging from 5% to 15% by weight relative to the total weight of solids of the dye powder.

10. The process according to claim 1, wherein the tannic acid or a gallotannin derivative thereof, or mixtures thereof, is present in the dye powder in a tannic acid or gallotannin derivative/anthocyan weight ratio ranging from 0.1/1 to 10/1.

11. The process according to claim 1, wherein the anthocyan is present in the dye powder in a content ranging from 0.05% to 50% by weight relative to the total weight of solids of the dye powder and the tannic acid or a gallotannin derivative thereof, or mixtures thereof, is present in the dye powder in a tannic acid or gallotannin derivative/anthocyan weight ratio ranging from 0.05/1 to 20/1.

12. The process according to claim 1, wherein the anthocyan is present in the dye powder in a content ranging from 0.3% to 25% by weight relative to the total weight of solids of the dye powder and the tannic acid or a gallotannin derivative thereof, or mixtures thereof, is present in the dye powder in a tannic acid or gallotannin derivative/anthocyan weight ratio ranging from 0.1/1 to 10/1.

13. The process according to claim 12, wherein the anthocyan is present in the dye powder in a content ranging from 5% to 15% by weight relative to the total weight of solids of the dye powder.

* * * * *